United States Patent [19]

Antoncic et al.

[11] Patent Number: 4,769,465

[45] Date of Patent: Sep. 6, 1988

[54] PROCESS FOR THE PREPARATION OF 2-(N-BENZYL-N-METHYLAMINO)-ETHYL METHYL 2,6-DIMETHYL-4-(M-NITROPHENYL)-1,4-DIHYDROPYRIDINE-3,5-DICARBOXYLATE AND ITS HYDROCHLORIDE SALT

[75] Inventors: Ljubo Antoncic; Iztok Jazbec; Darko Kocjan, all of Ljubljana; Ivana Krivec, Radomlje, all of Yugoslavia

[73] Assignee: LEK, tovarna farmacevtskih in kemicnih izdelkov, n.sol.o., Ljublijana, Yugoslavia

[21] Appl. No.: 862,938

[22] Filed: May 14, 1986

[51] Int. Cl.$^4$ .............................. C07D 211/90
[52] U.S. Cl. ........................................ 546/321
[58] Field of Search .......................... 546/321

[56] References Cited

U.S. PATENT DOCUMENTS

| | | | |
|---|---|---|---|
| 3,905,970 | 9/1975 | Bossert et al. | 546/321 |
| 3,974,275 | 8/1976 | Bossert et al. | 546/321 |
| 3,996,234 | 12/1976 | Bossert et al. | 546/321 |
| 4,285,955 | 8/1981 | Wehinger et al. | 546/321 |
| 4,483,985 | 11/1984 | Wehinger et al. | 546/321 |
| 4,551,467 | 11/1985 | Wehinger et al. | 546/321 |
| 4,672,068 | 6/1987 | Kutsuma et al. | 546/321 |

OTHER PUBLICATIONS

Meyer et al., Arzneim.-Forsch./Drug Res. 31(I), Nr 3(1981), pp. 407–409.
Glickman et al., JACS vol. 67, (1945), pp. 1017–1020.
Shibanuma et al., Chem. Pharm. Bull., 28(9), pp. 2809–2812, (1980).
Angew. Chem. 1978, 90(7), pp. 556–557.
Chem. Abstracts 87:108543f.

*Primary Examiner*—John M. Ford
*Assistant Examiner*—Dale A. Bjorkman
*Attorney, Agent, or Firm*—Pollock, Vande Sande & Priddy

[57] ABSTRACT

A new, technologically easily feasible process for the preparation of 2-(N-benzyl-N-methylamino)ethyl methyl 2,6-dimethyl-4-(m-nitrophenyl)-1,4-dihydropyridine-3,5-dicarboxylate, comprising a partrial hydrolysis of dimethyl 2,6-dimethyl-4-(m-nitrophenyl)-1,4-dihydropyridine-3,5-dicarboxylate in an inert organic solvent at a temperature between room temperature and the reflux temperature of the reaction mixture with an aqueous solution of alkali hydroxide and the reaction of the obtained 3-methoxycarbonyl-2,6-dimethyl-4-(m-nitrophenyl)-1,4-dihydropyridine-5-carboxylic acid either with N-(2-hydroxyethyl)-N-benzyl-methylamine in the presence or absence of an organic solvent in the presence of N,N'-dicyclohexylcarbodiimide at a temperature of between 25° and 120° C. or with N-(2-haloethyl)-N-benzyl-methylamine in the presence of an inert organic solvent and of a proton acceptor at a temperature of between 25° and 140° C., to yield the title compound, which can be, if desired, converted to its hydrochloride salt. The hydrochloride salt is known under the generic name "nicardipine hydrochloride" and is used as a valuable therapeutic in the therapy of cerebral insufficiency.

9 Claims, No Drawings

PROCESS FOR THE PREPARATION OF 2-(N-BENZYL-N-METHYLAMINO)-ETHYL METHYL 2,6-DIMETHYL-4-(M-NITROPHENYL)-1,4-DIHYDROPYRIDINE-3,5-DICARBOXYLATE AND ITS HYDROCHLORIDE SALT

TECHNICAL FIELD OF THE INVENTION

The present invention relates to a new process for the preparation of 2-(N-benzyl-N-methylamino)-ethyl methyl 2,6-dimethyl-4-(m-nitrophenyl)-1,4-dihydropyridine-3,5-dicarboxylate of the formula

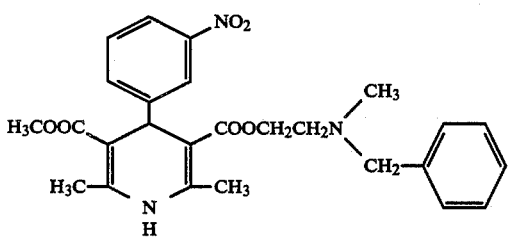

and its hydrochloride salt. This substance is known under the generic name nicardipine as well as under the designation YC-93. Nicardipine is a cerebral and coronary vasodilator and it is particularly used in the therapy of cerebral insufficiency.

Technical Problem

There exists a constant need to prepare nicardipine according to a technologically easily feasible process, which would give the desired substance in a good overall yield and in good purity without time-consuming chromatographic purifications of intermediates and of the end product resp. and without high-vacuum fractional distillation.

Prior Art

Nicardipine was disclosed as a new substance, which is particularly active as a cerebral vasodilator, for the first time in German Pat. No. 24 07 115 and in its equivalent U.S. Pat. No. 3,985,758. In this patent there were described several methods for synthetizing nicardipine, shown in Scheme I. A drawback of said methods are very poor overall yields of nicardipine. Besides, in order to obtain high purity nicardipine, the latter and its intermediates must be purified by column chromatography or by high vacuum fractional distillation. The poor overall yield of nicardipine is affected by the preparation of intermediates such as 2-(N-benzyl-N-methylamino)-ethyl acetoacetate, which is obtained in an exacting way and in a very poor yield of 10.5% by reacting 2-(N-benzyl-N-methylamino)-ethanol with ethyl acetoacetate in an anhydrous medium (M. Iwanami et al., Chem. Pharm. Bull. 27(6), 1426–1440 (1979)). The overall yield of nicardipine obtained in accordance with the method described in German patent 24 07 115 is between 2 and 12%. In Example 7 of said German patent there is described the most advantageous way, which avoids the use of intermediates of difficult access and wherein nicardipine is obtained in an overall yield of approximately 12% by reacting the intermediate chloroethyl methyl 2,6-dimethyl-4-(m-nitrophenyl)-1,4-dihydropyridine-3,5-dicarboxylate with N-methyl benzylamine.

SCHEME I

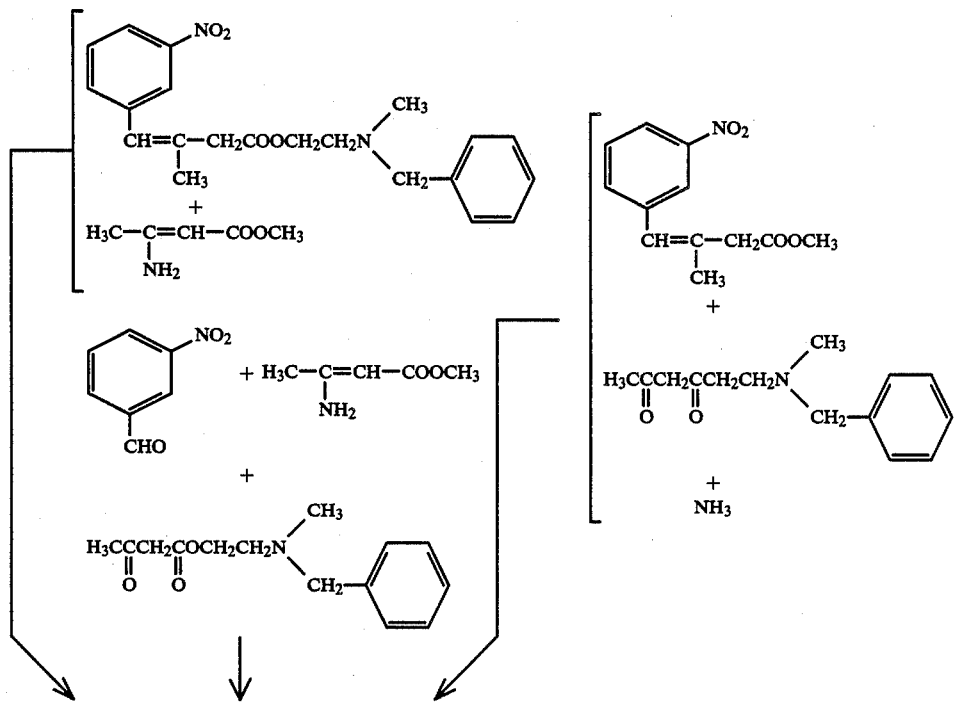

-continued
SCHEME I

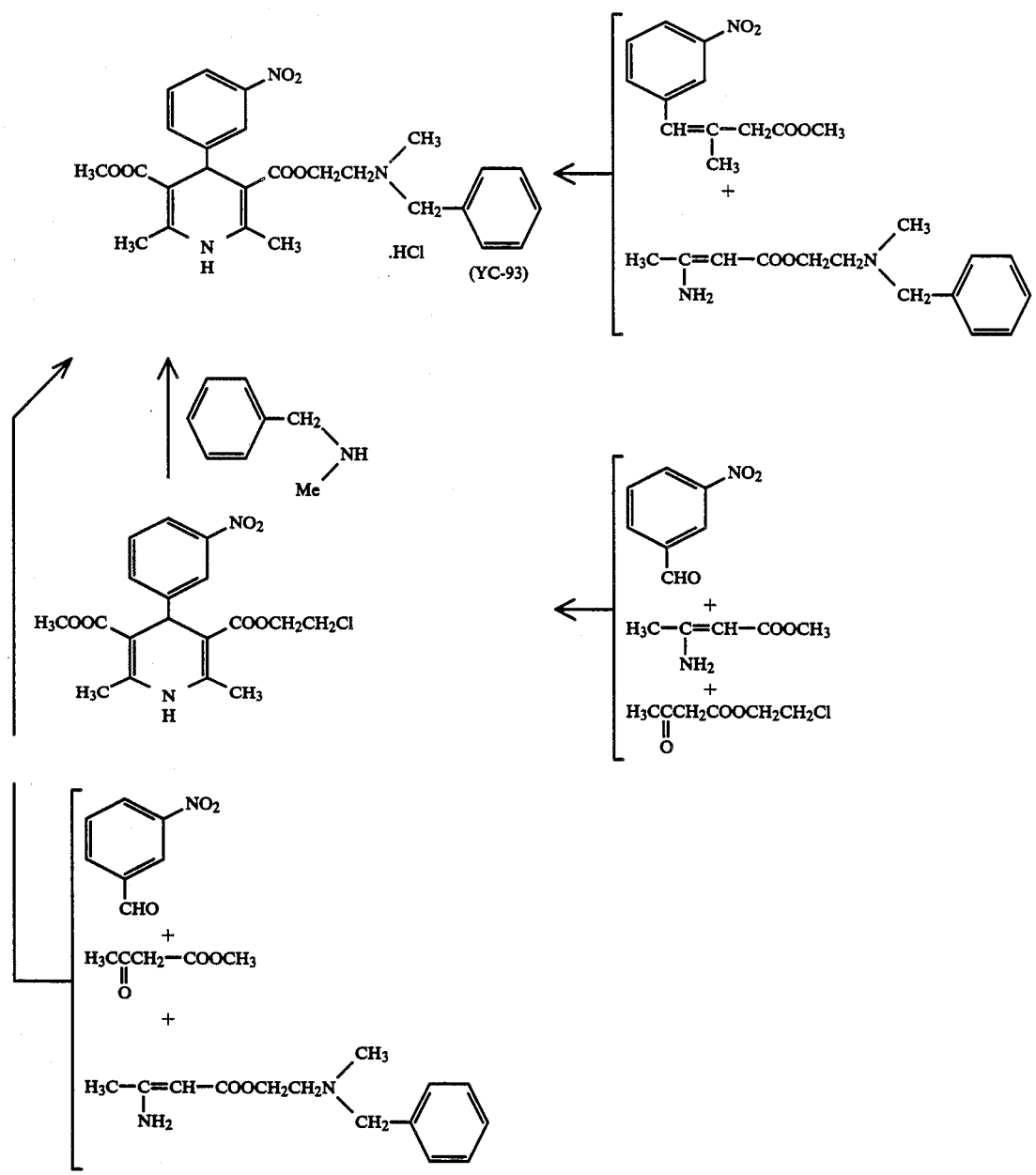

It is known that N-aryl- or N-alkyl-substituted dihydropyridine-3,5-dicarboxylates are easily hydrolyzed under the action of alkalis to the corresponding dihydropyridine-monocarboxylic acids (A. Sausins et al., Khim. Geterocikl. Soedin., 2, 272 (1978)). Contrary to the easy alkaline hydrolysis of N-aryl- and N-alkyl-substituted dihydropyridine-3,5-dicarboxylates, the N-unsubstituted dihydropyridine-3,5-dicarboxylates are not at all or only to a very small extent hydrolyzed to the corresponding monoesters of dicarboxylic acids (N. Eisner et al., Chem. Rev. 72, 1, 4 (1972) or B. Loev et al., J. Heterocyclic Chem. 12, 363 (1975)). As reported by M. Iwanami et al., Chem. Pharm. Bull. 27(6), 1426–1440 (1979), and T. Shibanuma, Chem. Pharm. Bull., 28(9) 2809–2812 (1980), somewhat better results of the partial hydrolysis can be achieved in the manner shown in the following Scheme II.

SCHEME II

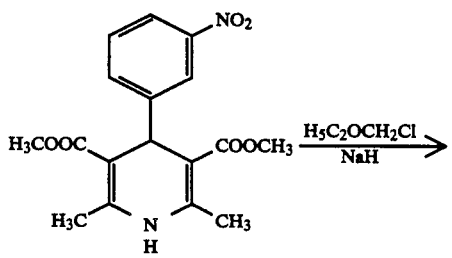

-continued
SCHEME II

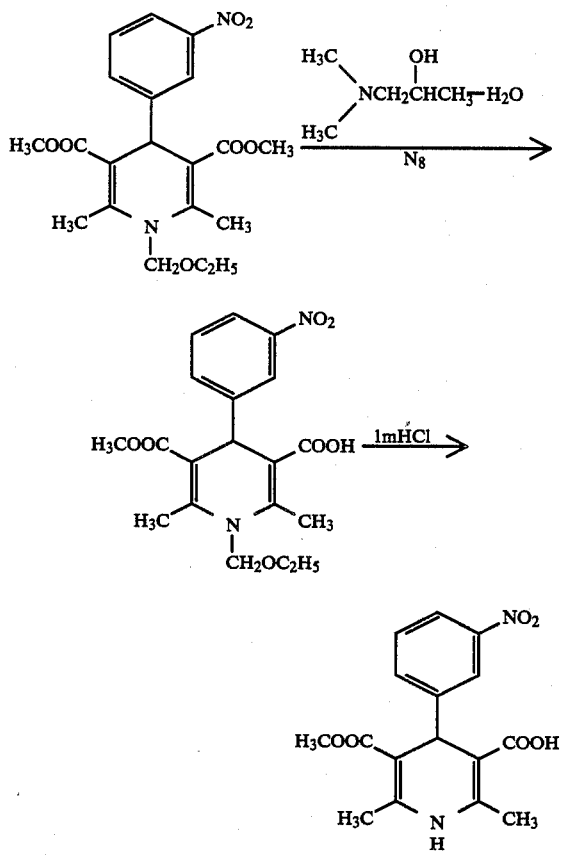

In this procedure an ethoxymethyl group is introduced at the position 1 of the nucleus of the dihydropyridine dicarboxylate, yielding dimethyl 1-ethoxymethyl-2,6-dimethyl-4-(m-nitrophenyl)-1,4-dihydropyridine-3,5-dicarboxylate, which is then hydrolyzed in a manner known per se with 1-dimethylamino-2-propanol containing approximately 2% of water to the corresponding monoester of the dicarboxylic acid (yield approx. 43%), which in turn is subjected to mild hydrolysis in order to remove the ethoxymethyl group, whereby 3-methoxycarbonyl-2,6-dimethyl-4-(m-nitrophenyl)-1,4-dihydropyridine-5-carboxylic acid is obtained. Yet the process is time-consuming and the yields are not satisfactory.

Description of the Solution of the Technical Problem with Examples

It has now been surprisingly found that 3-methoxycarbonyl-2,6-dimethyl-4-(m-nitrophenyl)-1,4-dihydropyridine-5-carboxylic acid, which is used as a key intermediate in the synthesis of nicardipine according to the invention, can be obtained in a good yield by the partial hydrolysis of dimethyl 2,6-dimethyl-4-(m-nitrophenyl)-1,4-dihydropyridine-3,5-dicarboxylate with an aqueous solution of alkali hydroxides, such as lithium or sodium hydroxide hydrate, in the presence of lower alcohols, such as methanol, as inert organic solvents, at a temperature of between room temperature and reflux temperature of the reaction mixture. The alkali hydroxide is used in excess.

This partial hydrolysis of the starting compound, i.e. of N-unsubstituted dihydropyridine dicarboxylate, which proceeds easily and with a good yield, was indeed suprising and unexpected with respect to the Prior Art, since according to the known literature sources one would have expected that the partial hydrolysis of the starting dimethyl 2,6-dimethyl-4-(m-nitrophenyl)-1,4-dihydropyridine-3,5-dicarboxylate would not take place at all. Dimethyl 2,6-dimethyl-4-(m-nitrophenyl)-1,4-dihydropyridine-3,5-dicarboxylate, which is used in the nicardipine synthesis according to the invention as a starting compound, is a known substance and can be prepared in a good yield by Hantzsch' method for the synthesis of 1,4-dihydropyridines by reacting 3-nitrobenzaldehyde, methyl acetoacetate and ammonia at the reflux temperature of the reaction mixture in the presence of an inert organic solvent.

The second key intermediate in the synthesis of nicardipine according to the invention is N-(2-hydroxyethyl)-N-benzyl-methylamine of the formula

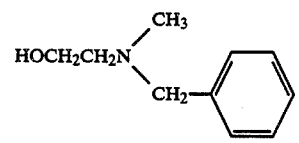

and N-(2-haloethyl)-N-benzyl-methylamine of the formula

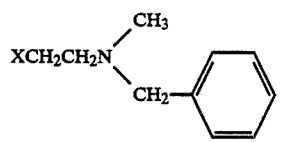

wherein X stands for halo, such as chloro or bromo, resp.

N-(2-hydroxyethyl)-N-benzyl-methylamine is a known compound and is described in literature (J. Am. Chem. Soc. 76, 4920–23, 1954). The reaction of this compound with thionyl chloride gives N-(2-chloroethyl)-N-benzyl-methylamine in a good yield. This compound can also be prepared by reacting N-benzyl-methylamine with 1-bromo-2-chloroethane, the yields, however, are poor and the dimeric 1,2-bis(N-benzylmethylamino)ethane, which is formed as a by-product, must be separated by chromatography.

According to the invention the two key intermediate compounds, i.e. 3-methoxycarbonyl-2,6-dimethyl-4-(m-nitrophenyl)-1,4-dihydropyridine-5-carboxylic acid of the formula

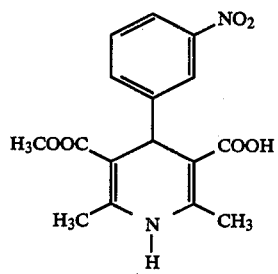

and either (a) N-(2-hydroxyethyl)-N-benzyl-methylamine of the formula

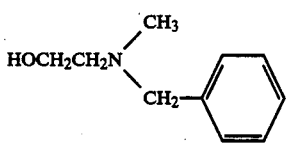

in the presence or in the absence of an organic solvent and in the presence of N,N'-dicyclohexylcarbodiimide (DCC) as condensing agent at a temperature of between 25° and 120° C., or (b) N-(2-haloethyl)-N-benzyl-methylamine of the formula

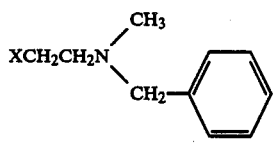

wherein X stands for halo, such as chloro or bromo, in the presence of inert organic solvents and of an organic or inorganic base as proton acceptor at a temperature of between 25° and 140° C., are reacted to yield 2-(N-benzyl-N-methylamino)-ethyl methyl 2,6-dimethyl-4-(m-nitrophenyl)-1,4-dihydropyridine-3,5-dicarboxylate, which can be converted to its hydrochloride salt (nicardipine hydrochloride) in a manner known per se.

This compound can be isolated in two crystal forms (alpha form and beta form), which differ in the melting point, IR spectrum and X-ray diffraction pattern as reported in the above-mentioned German patent and by M. Iwanami et al., Chem. Pharm. Bull. 27(6), 1426–1440 (1979).

Lower alcohols, such as n-butanol, can be used as inert solvents and an inorganic or organic base, such as triethylamine, can be used as the proton acceptor.

The overall yield of nicardipine hydrochloride amounts to 46% in the variant (a) and to 29% in the variant (b), with respect to the starting materials.

The process of the invention is shown in Scheme III.

In this scheme there is also shown the process variant, wherein the intermediate 3-methoxycarbonyl-2,6-dimethyl-4-(m-nitrophenyl)-1,4-dihydropyridine-5-carboxylic acid is reacted with 1-bromo-2-chloroethane. In this variant, however, the yields are poor and the dimeric by-product 1,2-bis(N-benzylmethylamino)ethane must be separated by chromatography. The obtained chloroethyl methyl 2,6-dimethyl-4-(m-nitrophenyl)-1,4-dihydropyridine-3,5-dicarboxylate can be converted to nicardipine or its hydrochloride in the manner described in German patent 24 07 115 (Example 7).

The reactions of the starting compounds with 1-bromo-2-chloroethane, which give worse results, are shown merely by way of illustration.

SCHEME III

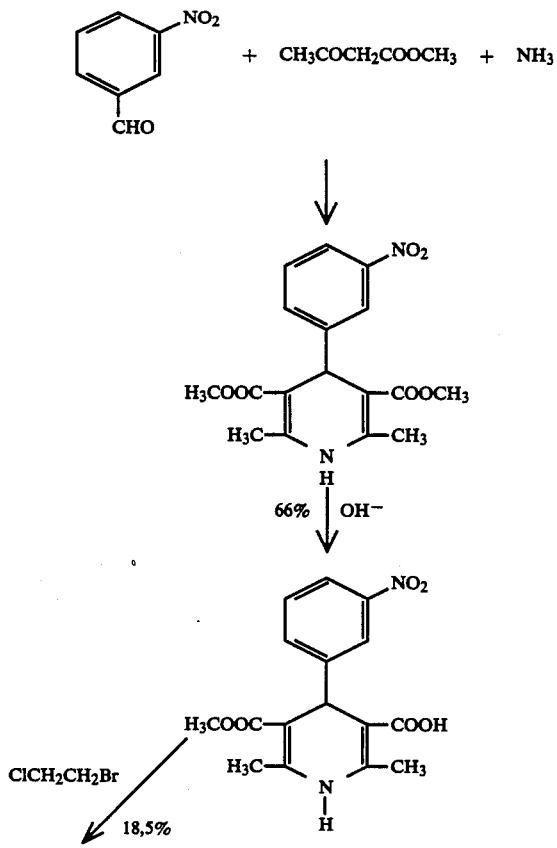

SCHEME III

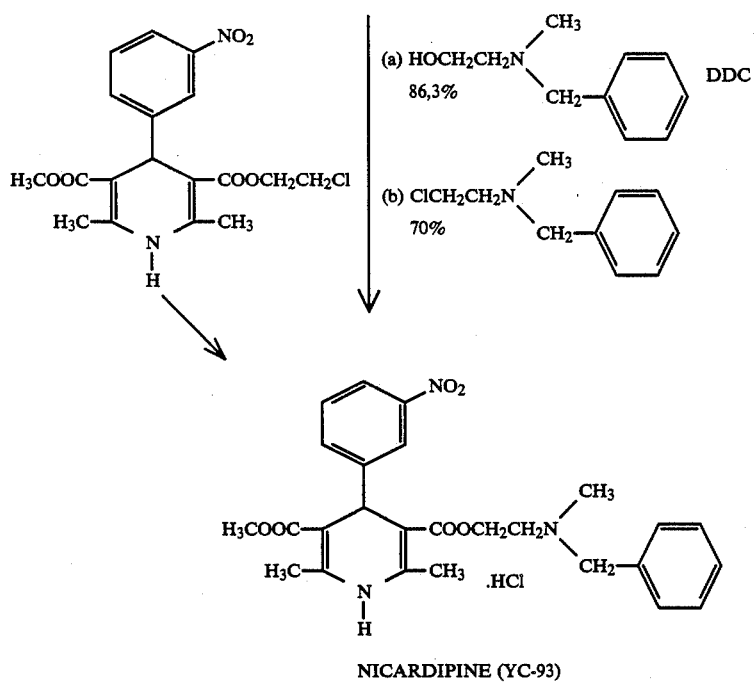

NICARDIPINE (YC-93)

The invention is illustrated by the following non-limiting Examples.

EXAMPLE 1

(a) N-(2-chloroethyl)-N-benzylmethylamine

I. To a solution of N-(2-hydroxyethyl)-N-benzylmethylamine (16.5 g, 0.1 mole) in chloroform (100 ml), thionyl chloride (13 g, 0.11 mole) is added at room temperature under stirring and exclusion of atmospheric moisture. The reaction mixture is heated to reflux temperature and stirred at this temperature for 30 more minutes. The reaction mixture is washed with a 10% aqueous solution of $NaHCO_3$ ($3\times200$ ml) and with water ($2\times200$ ml). The organic layer is dried with anhydrous $Na_2SO_4$, the drying agent is removed and the filtrate is evaporated to dryness.

Thus, there is obtained the title compound (14.3 g, 78%) in the form of an oily residue.

Empirical formula: $C_{10}H_{14}NCl$
Molecular Weight: 183
NMR ($CDCl_3$) δ: 2.4 (3H, s, >N—$CH_3$) 2.8 (2H, t, >N—$CH_2CH_2$—) 3.65 (2H, t, >N—$CH_2C\underline{H}_2$—) 3.7 (2H, s, $\overline{C_6H_5}$—$C\underline{H}_2$—)

II. A solution of N-benzyl-methylamine (12.1 g, 0.1 mole), 1-bromo-2-chloroethane (14.3 g, 0.1 mole) and triethylamine (14 g, 0.14 mole) in toluene (100 ml) is stirred at the reflux temperature of the reaction mixture for 4 hours. The organic solvent is evaporated and the oily residue is dissolved in a small amount of an ethyl acetate/methanol/ammonia (80:30:3) mixture and subjected to chromatography on a silica gel column ($4\times35$ cm) in order to separate the two products obtained.

Thus, there are obtained N-(2-chloroethyl)-N-benzylmethylamine (2 g, 10.9%) and the dimeric 1,2-bis-(N-benzylmethylamino)ethane (4 g, 14.9%) as oily substances.

Empiric formula: $C_{10}H_{14}NCl$
Molecular weight: 183

NMR ($CDCl_3$) of the title compound: δ: 2.4 (3H, s, >N—$CH_3$), 2.8 (2H, t, >N—$CH_2CH_2$—), 3.65 (2H, t, >N—$CH_2C\underline{H}_2$—), 3.7 (2H, s, $\overline{C_6H_5}$—$C\underline{H}_2$—).

NMR ($CD\overline{Cl}_3$) of the dimeric compound: δ: 2.2 (3H, s, >N—$CH_3$), 2.6 (4H, s, >N—$CH_2CH_2$—N<), 3.55 (2H, s, $C_6H_5$—$C\underline{H}_2$).

(b)
3-methoxycarbonyl-2,6-dimethyl-4-(m-nitrophenyl)-1,4-dihydropyridine-5-carboxylic acid Dimethyl 2,6-dimethyl-4-(m-nitrophenyl)-1,4-dihydropyridine-3,5-dicarboxylate (17.3 g, 0.05 mole) is suspended in methanol (280 ml) and thereto a solution of NaOH (15.9 g, 0.4 mole) in water (52 ml) is added at room temperature under stirring. The reaction mixture is stirred at reflux temperature for 5 hours, cooled, water (1050 ml) is added under stirring and the resulting mixture is filtered. The precipitate is the unreacted starting compound, i.e. dimethyl 2,6-dimethyl-4-(m-nitrophenyl)-1,4-dihydropyridine-3,5-dicarboxylate. To the clear filtrate activated carbon (1 g) is added and the mixture is stirred at 50°–60° C. for 30 minutes. After cooling the activated carbon is filtered off, the filtrate is acidified with 1 n HCl to pH 2.5 and the precipitate is filtered and washed with water ($2\times15$ ml). Thus, there is obtained the pure title compound (11 g, 66%), m.p. 202°–206° C.

Empiric formula: $C_{16}H_{16}N_2O_6$ Molecular weight: 332
NMR (DMSO-$d_6$) δ: 2.4 (6H, s, $C_{2,6}$—$CH_3$), 3.6 (3H, s, —$COOCH_3$), 5.1 (1H, s, $C_4$—H), 9 (1H, s, >N—H).

(c) 2-(N-benzyl-N-methylamino)ethyl methyl 2,6-dimethyl-4-(m-nitrophenyl)-1,4-dihydropyridine-3,5-dicarboxylate hydrochloride (nicardipine hydrochloride)

(A) A solution of 3-methoxycarbonyl-2,6-dimethyl-4-(m-nitrophenyl)-1,4-dihydropyridine-5-carboxylic acid (3.32 g, 0.01 mole), N-(2-chloroethyl)-N-benzylmethylamine (1.83 g, 0.01 mole) and triethylamine (1.41 g, 0.014 mole) in n-butanol (60 ml) is heated for 2 hours to 120° C. The reaction mixture is evaporated to an oily residue containing crude 2-(N-benzyl-N-methylamino)ethyl methyl 2,6-dimethyl-4-(m-nitrophenyl)-1,4-dihydropyridine-3,5-dicarboxylate (nicardipine-base).

The obtained oily residue is dissolved in chloroform (22.2 ml), washed with 10% hydrochloric acid (16.0 ml) and with water (3×10 ml). The organic layer is dried with anhydrous Na$_2$SO$_4$ and the solvent is evaporated under reduced pressure. The oily residue is dissolved in ethyl acetate (17 ml) and stirred at 0° C. for 2 hours. The precipitate, which separates, is filtered off, dried in vacuo and recrystallized from acetone. Thus, there is obtained the desired product nicardipine hydrochloride (3.6 g, 70.0%), m.p. 129°–132° C. (with decomposition).

Hydrochloride:
Empirical formula: C$_{26}$H$_{30}$N$_3$O$_6$Cl
Molecular weight: 515
NMR (base) (DMSO-d$_6$):

(B) A mixture of 3-methoxycarbonyl-2,6-dimethyl-4-(m-nitrophenyl)-1,4-dihydropyridine-5-carboxylic acid (3.32 g, 0.01 mole), N-(2-hydroxyethyl)-N-benzylmethylamine (4.98 g) and N,N'-dicyclohexylcarbodiimide (DCC) (2.05 g) is stirred at 60°–80° C. for 1 hour. To the reaction mixture chloroform (16 ml) is added and the mixture is washed with water (3×50 ml). Then the organic layer is washed with a 10% aqueous solution of HCl (16 ml) and water (3×10 ml). The organic layer is dried with anhydrous Na$_2$SO$_4$ and the solvent is evaporated in vacuo. The oily residue is dissolved in ethyl acetate (18 ml) and stirred at 0° C. for 2 hours. The precipitate, which separates, is filtered off, dried in vacuo and recrystallized from acetone. Thus, there is obtained the title compound nicardipine hydrochloride (4.4 g, 85.4%).

EXAMPLE 2

Chloroethyl methyl 2,6-dimethyl-4-(m-nitrophenyl)-1,4-dihydropyridine-3,5-dicarboxylate A mixture of 3-methoxycarbonyl-2,6-dimethyl-4-(m-nitrophenyl)-1,4-dihydropyridine-5-carboxylic acid (3.32 g, 0.01 mole), 1-bromo-2-chloroethane (1.43 g, 0.01 mole) and triethylamine (1.01 g, 0.01 mole) is stirred at 120° C. for 8 hours. The reaction mixture is dissolved in a mixture of ethyl acetate/methanol/ammonia (80:30:3) and subjected to chromatography on a silica gel column (2×35 cm). Thus, there are obtained chloroethyl methyl 2,6-dimethyl-4-(m-nitrophenyl)-1,4-dihydropyridine-3,5-dicarboxylate (0.75 g, 19.8%) and the dimeric ethylene glycol-di-/2,6-dimethyl-4-(m-nitrophenyl)-5-methoxycarbonyl-1,4-dihydropyridyl-3/dicarboxylate (0.1 g, 1.5%) as oily substance.

Empirical formula: C$_{18}$H$_{19}$ClN$_2$O$_6$
Molecular weight: 394
NMR (CDCl$_3$) of the title compound:

NMR (CDCl$_3$) of the dimeric compound:

The title compound can be converted to nicardipine and its hydrochloride as described in German patent 24 07 115 (Example 7).

What is claimed is:

1. A process for the preparation of 2-(N-benzyl-N-methylamino)ethyl methyl 2,6-dimethyl-4-(m-nitrophenyl)-1,4-dihydropyridine-3,5-dicarboxylate of the formula

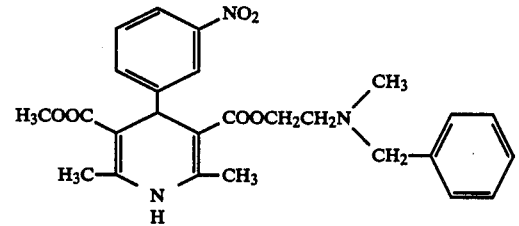

and of its hydrochloride salt, characterized in that dimethyl 2,6-dimethyl-4-(m-nitrophenyl)-1,4-dihydropyridine-3,5-dicarboxylate is partially hydrolyzed in the presence of inert organic solvents at a temperature of between room temperature and the reflux temperature of the reaction mixture with an aqueous solution of alkali hydroxides to 3-methoxycarbonyl-2,6-dimethyl-4-(m-nitrophenyl)-1,4-dihydropyridine-5-carboxylic acid of the formula

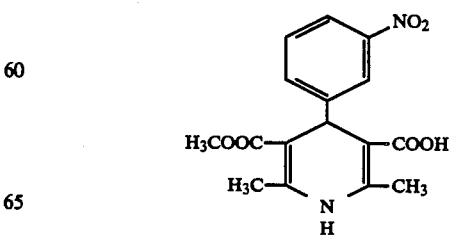

which is reacted either (a) with N-(2-hydroxyethyl)-N-benzyl-methylamine of the formula

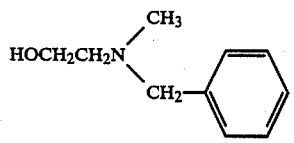

in the presence or absence of an organic solvent and in the presence of N,N'-dicyclohexylcarbodiimide at a temperature of between 25° and 120° C. or (b) with N-(2-haloethyl)-N-benzyl-methyl amine of the formula

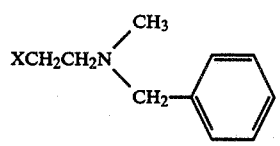

wherein X stand for halo, in the presence of inert organic solvent and proton acceptor at a temperature of between 25° and 140° C., to yield the title compound, which is, if desired, converted to its pharmaceutically acceptable hydrochloride salt.

2. A process according to claim 1, characterized in that the partial hydrolysis is effected in the presence of an aqueous solution of sodium hydroxide.

3. A process according to claim 1, characterized in that a lower alcohol is used as the inert organic solvent in the partial hydrolysis.

4. A process according to claim 1, characeized in that a lower alcohol is used as the inert organic solvent in the reaction with N-(2-haloethyl)-N-benzyl-methyl amine.

5. A process according to claim 1, characterized in that an organic base is used as the proton acceptor.

6. The process of claim 1 wherein X is chloro or bromo.

7. The process of claim 3 wherein said alcohol is methanol.

8. The process of claim 4 wherein said lower alcohol is n-butanol.

9. The process of claim 5 wherein said organic base is triethylamine.